(12) United States Patent
Rossmoore

(10) Patent No.: US 7,147,824 B2
(45) Date of Patent: Dec. 12, 2006

(54) METHOD FOR SUPPRESSING GROWTH OF MYCOBACTERIA IN METALWORKING FLUIDS

(76) Inventor: Harold W. Rossmoore, 6548 Pleasant Lake Ct., West Bloomfield, MI (US) 48322

( * ) Notice: Subject to any disclaimer, the term of this patent is extended or adjusted under 35 U.S.C. 154(b) by 0 days.

(21) Appl. No.: 11/242,293

(22) Filed: Oct. 3, 2005

(65) Prior Publication Data
US 2006/0032824 A1  Feb. 16, 2006

Related U.S. Application Data

(62) Division of application No. 10/420,161, filed on Apr. 22, 2003, now Pat. No. 6,951,618.

(51) Int. Cl.
*C10M 129/42* (2006.01)
(52) U.S. Cl. .................. 422/37; 210/755; 210/764; 508/242; 508/271; 514/372; 514/499
(58) Field of Classification Search ............. 508/242, 508/271
See application file for complete search history.

(56) References Cited

U.S. PATENT DOCUMENTS

| | | | |
|---|---|---|---|
| 3,523,121 A | 8/1970 | Lewis et al. | |
| 3,761,488 A | 9/1973 | Lewis et al. | |
| 3,957,808 A | 5/1976 | Miller et al. | |
| 4,055,655 A | 10/1977 | Maurer et al. | |
| 4,105,431 A | 8/1978 | Lewis et al. | |
| 4,129,509 A | 12/1978 | Shringarpurey et al. | |
| 4,180,473 A | 12/1979 | Maurer et al. | |
| 4,243,403 A | 1/1981 | Lewis et al. | |
| 4,252,694 A | 2/1981 | Lewis et al. | |
| 4,265,899 A | 5/1981 | Lewis et al. | |
| 4,278,610 A | 7/1981 | Maurer et al. | |
| 4,279,762 A | 7/1981 | Lewis et al. | |
| 4,608,183 A | 8/1986 | Rossmoore | |
| 4,707,282 A * | 11/1987 | Rossmoore | 508/257 |
| 5,364,649 A * | 11/1994 | Rossmoore et al. | 424/637 |
| 6,712,975 B1 * | 3/2004 | Gonzalez et al. | 210/668 |

OTHER PUBLICATIONS

Willingham and Derbyshire, J. Soc. Tribol. Lub. Eng. 47: 729-732 (1991).
Shelton et al,, Emerg. Infect. Dis 5: 270-273 (1999).
Moore et al., AIHJ 62: 205-213 (2000).
Wilson et al., Int. J. Syst. Evol. Microbiol. 51: 1751-1764 (2001).
Rossmoore, Intl. Biodeter. 26: 225-235 (1990).
Sondossi et al., Intl. Biodeter. Biodeg. 32: 243-261 (1993).
Wallace, Jr. et al., Appl. Environ. Microbiol. 68: 5580-5584 (2002).
Telenti et al., J. Clin. Microbiol. 31: 175-178 (1993).
Wallace Jr. et al., J. Clin. Microbiol. 31: 2697-2701 (1993).
Wallace Jr. et al., J. Clin. Microbiol. 31: 3231-3239 (1993).
Steingrube et al., J. Clin. Microbiol. 33: 149-153 (1995).

* cited by examiner

*Primary Examiner*—Peter A. Hruskoci
(74) *Attorney, Agent, or Firm*—Ian C. McLeod

(57) ABSTRACT

A method for suppressing the growth of mycobacteria associated with hypersensitivity pneumonitis, in particular *Mycobacterium immunogenum*, in metalworking fluids is described. The method uses antimicrobial or biocidal compositions which include a metal complex comprising disodium monocopper (II) citrate and an isothiazolone mixture preferably comprising 5-chloro-2-methyl-4-isothiazolin-3-one 2-methyl-4-isothiazolin-3-one. Also described are methods for detecting and identifying the mycobacteria.

5 Claims, 1 Drawing Sheet

METHOD FOR SUPPRESSING GROWTH OF MYCOBACTERIA IN METALWORKING FLUIDS

CROSS-REFERENCE TO RELATED APPLICATION

This application is a divisional of application(s) application Ser. No. 10/420,161 file on Apr.22, 2003.

STATEMENT REGARDING FEDERALLY SPONSORED RESEARCH OR DEVELOPMENT

Not applicable.

Reference to a "Computer Listing Appendix submitted on a Compact Disc"

Not Applicable.

BACKGROUND OF THE INVENTION (1) Field of the Invention

The present invention relates to a method for suppressing the growth of mycobacteria associated with hypersensitivity pneumonitis, in particular *Mycobacterium immunogenum*, in metalworking fluids. The method uses synergistic antimicrobial or biocidal compositions which include a metal complex comprising disodium monocopper (II) citrate and an isothiazolone mixture preferably comprising 5-chloro-2-methyl-4-isothiazolin-3-one and 2-methyl-4-isothiazolin-3-one. The present invention also relates to methods for detecting and identifying the mycobacteria.

(2) Description of Related Art

The prior art has described metal complexes of organic ligands as antimicrobial or biocidal compounds. These include U.S. Pat. No. 4,055,655 to Maurer et al., U.S. Pat. No. 4,129,589 to Shringarpurey et al., and U.S. Pat. No. 4,180,473 to Maurer et al. The process for their manufacture is described in U.S. Pat. No. 4,278,610 to Maurer et al. The problem is that these compounds are relatively poor antimicrobials and even large amounts provided protection for only a limited period of time.

The isothiazolones are described in U.S. Pat. No. 3,523,121 to Lewis et al.; U.S. Pat. No. 3,761,488 to Lewis et al.; U.S. Pat. No. 3,957,808 to Miller et al.; U.S. Pat. No. 4,105,431 to Lewis et al.; U.S. Pat. No. 4,243,403 to Lewis et al.; U.S. Pat. No. 4,252,694 to Lewis et al.; U.S. Pat. No. 4,265,899 to Lewis et al.; U.S. Pat. No. 4,279,762 to Lewis et al. These are very superior antimicrobial agents; however, relatively large amounts are required. Compatibility and stabilization of isothiazolones in metalworking fluids (MWF) has been described by Willingham and Derbyshire, J. Soc. Tribol. Lub. Eng. 47: 729–732 (1991).

Disodium monocopper (II) citrate (MCC) is particularly described as an antimicrobial compound by U.S. Pat. No. 4,055,655. Metalworking fluid (MWF) stabilizing activity is described in U.S. Pat. No. 4,129,509 (1978)). The former patent states that the compound is effective against microorganisms growing in alkaline environments (pH 8–12) due to the stability of the metal complex form only at high pH, with dissociation into toxic copper ions occurring upon encountering the lower pH (7.0) within microbial cells.

Studies on MCC have shown that it can temporarily inhibit the growth of *Pseudomonas aeruginosa* in laboratory media and transiently reduce the cell count in MWF contaminated with *Pseudomonas* spp. The use of MCC as a MWF additive is becoming more widespread and an improvement in its effectiveness was needed.

Although bacteria are highly important in the biodeterioration of MWF, fungi and yeast can play a major role as well, especially in the synthetic fluids (Bennett, Prog. Indust. Microbiol., 13: 121 (1974)), (Rossmoore and Holtzman, Dev. Indust. Microbiol., 15: 273–280 (1974)). *Fusarium* and *Cephalosporium* are prominent fungal contaminants, and among the yeasts, *Candida* and *Trichosporon* spp. are often isolated. Fungi and yeast are known to be sensitive to the toxic effects of Cu ion (Hugo and Russell, In: Principles and Practices of Disinfection, Preservation and Sterilization, Russell et al. (Eds.), Blackwell Scientific Publications, Boston, p. 69 (1982)) and consequently the effect of MCC at high pH on a representative yeast, *Candida tropicalis*, was studied.

As a result of the machining operation itself, MWF can become contaminated with selectively large concentrations of soluble iron. The high stability constant of ferric citrate can allow exchange reactions between the ferric and copper ions in binding to the citrate ligand (Ashcroft and Mortimer, Thermochemistry of Transition Metal Complexes, Academic Press, New York (1970)). Such reactions may destroy the antimicrobial activity of MCC in alkaline environments.

KATHON 886 is a commercial antimicrobial solution which is a mixture of 5-chloro-2-methyl-4-isothiazolin-3-one (8.6% by wt.) and 2-methyl-4-isothiazolin-3-one (2.6% by wt.). The mixture is very effective against bacteria, fungi and algae. The required dosages are sometimes ineffective in achieving the best results due to interfering nucleophiles in the metalworking fluids. The molecular species considered as nucleophiles in these systems are amines and sulfides, the former contributed by many metalworking fluid formulae and the latter from microbial activity. Thus, efficacy is a function of the metalworking fluid composition as well as the level of microbial contamination, nucleophiles from both competing for the isothiazolones.

An important improvement in methods for suppressing growth of microorganisms in MWFs was introduced by U.S. Pat. No. 4,608,183 to Rossmoore. The patent discloses novel antimicrobial or biocidal mixtures comprising disodium monocopper citrate (MCC) and a mixture of isothiazolones. The components in the mixture were found to synergistically suppress growth of many species of bacteria and fungi in MWF over a long period of time. The synergism has been described in Rossmoore, Intl. Biodeter. 26: 225–235 (1990) and Sondossi et al., Intl. Biodeter. Biodegr. 32: 243–261 (1993). The compositions are particularly useful for metal cutting fluids wherein long duration antimicrobial activity is desired.

Over the past decade, it has been recognized that MWFs can be contaminated with mycobacteria as well as bacteria and fungi. It was further recognized that high levels of mycobacteria in MWFs appeared to coincide with outbreaks of hypersensitivity pneumonitis (HP) in industrial machinists (Kreiss and Cox-Ganser, Am. J. Ind. Med. 32: 423–432 (1997); Shelton et al., Emerg. Infect. Dis. 5: 270–273 (1999); Moore et al., AIHJ 62: 205–213 (2000)). Recently, a newly described species of mycobacteria, *Mycobacobacterium immunogenum*, was identified in MWFs associated with outbreaks of HP (Wilson et al., Int. J. Syst. Evol. Microbiol. 51: 1751–1764 (2001). More recently, a single genotype of *Mycobacterium immunogenum* was discovered to be present in MWFs associated with HP (Wallace et al., Appl. Environ. Microbiol. 68: 5580–5584 (2002)). A sample of the *Mycobacterium immunogenum* isolated from MWF was deposited at the American Type Culture Collection, 10801 University Boulevard, Manassas, Va. as ATCC 700506 and the Deutsche Sammlung von Mikroorganismen und Zellkulturen GmbH, Braunschweig, Germany as DSMZ 8223. Outbreaks of HP has continued even though MWFs are routinely treated with biocides. Therefore, there is a need for a method for treating MWFs which will suppress growth in MWFs the *Mycobacterium immunogenum* genotype responsible for the HP outbreaks. Preferably, the method would suppress growth of other bacteria and fungi as well.

SUMMARY OF THE INVENTION

The present invention provides a method for suppressing the growth of mycobacteria associated with hypersensitivity pneumonitis, in particular *Mycobacterium immunogenum*, in metalworking fluids. The method uses synergistic antimicrobial or biocidal compositions which include a metal complex comprising disodium monocopper (II) citrate and an isothiazolone mixture preferably comprising 5-chloro-2-methyl-4-isothiazolin-3-one 2-methyl-4-isothiazolin-3-one. The present invention also provides a method for detecting and identifying the mycobacteria.

Therefore, the present invention provides a method for suppressing growth of mycobacteria associated with hypersensitivity pneumonitis in an industrial metalworking fluid which comprises (a) providing a composition comprising a copper complex comprising disodium monocopper (II) citrate and an isothiazolone mixture comprising 5-chloro-2-methyl-4-isothiazolin-3-one and 2-methyl-4-isothiazolin-3-one, wherein the copper complex provides copper ion to the metalworking fluid in an amount which maintains biocidal activity of the isothiazolone mixture; (b) adding the composition to the metalworking fluid in an amount which is sufficient to suppress the growth of the mycobacteria in the metalworking fluid for at least 48 hours; and (c) monitoring the metalworking fluid containing the composition for the mycobacteria.

The present invention further provides a method for suppressing growth of mycobacteria in a metalworking fluid which comprises (a) providing a copper complex comprising disodium monocopper (II) citrate and an isothiazolone mixture comprising 5-chloro-2-methyl-4-isothiazolin-3-one 2-methyl-4-isothiazolin-3-one, wherein the copper complex provides more than 250 ppm, preferably about 500 ppm, of copper ion to the metalworking fluid; (b) adding the copper complex and the isothiazolone mixture to the metalworking fluid wherein the metal complex and the isothiazolone mixture suppresses the growth of the mycobacteria in the metalworking fluid for at least 48 hours; and (c) monitoring the metalworking fluid containing the metal complex and isothiazolone for the mycobacteria.

In a further embodiment of the above methods, the copper complex is added to the metalworking fluid up to about 24 hours before the isothiazolone mixture is added to the metalworking fluid or the copper complex and the isothiazolone mixture are added to the metalworking fluid at the same time.

In a preferred embodiment of the above methods, the 5-chloro-2-methyl-4-isothiazolin-3-one and 2-methyl-4-isothiazolin-3-one are in a weight ratio of about 3 to 1. It is further preferable that the composition be mixed with the metalworking fluid to produce an amount of the isothiazolone mixture which is greater than about 7.5 ppm, preferably from about 15 ppm to about 21 ppm. The above methods are particularly efficacious against the mycobacteria *Mycobacterium immunogenum* which has a restriction fragment length polymorphism pattern produced by a DraI digest of *Mycobacterium immunogenum* DNA as shown in FIG. 1. In further embodiments, the copper complex provides more than 250 ppm, preferably about 500 ppm, copper ion to the metalworking fluid. The composition is efficacious even when introduced to MWFs in which the isothiazolone is incompatible with the metalworking fluid when the isothiazolone mixture is introduced into the metalworking fluid alone.

In a further embodiment of the above methods, the isothiazolone mixture comprises 5-chloro-2-methyl-4-isothiazolin-3-one 2-methyl-4-isothiazolin-3-one, wherein the isothiazolone mixture is present in an amount which is less than is required for biocidal activity when the mixture is introduced into the metalworking fluid alone. Preferably, the copper complex provides more than 250 ppm, preferably about 500 ppm, of copper ion to the metalworking fluid.

The present invention further provides a method for reducing a risk that a person in a metalworking environment will contract hypersensitivity pneumonitis caused by mycobacteria which is present in the environment, which comprises (a) providing a composition comprising a copper complex comprising disodium monocopper (II) citrate and an isothiazolone mixture; (b) adding the composition to metalworking fluids in the environment in an amount which is sufficient to suppress the growth of the mycobacteria in the metalworking fluid for at least 48 hours wherein the metalworking fluid containing the composition is monitored for the mycobacteria; and (c) exposing the person to the metalworking environment, wherein suppression of the growth of the micobacteria in the metalworking fluid by the composition reduces the risk that the person will contract the hypersensitivity pneumonitis.

The present invention further provides a method of industrial metal grinding for producing a shaped metal article which provides a reduced risk of hypersensitivity pneumonitis in a metal-grinding machinist, which comprises (a) applying a force to a metal workpiece with a grinding tool contacting the workpiece while supplying to the interface between the grinding tool and the workpiece a water-based metalworking fluid comprising a copper complex comprising disodium monocopper (II) citrate and an isothiazolone mixture wherein the metal complex and the isothiazolone mixture is in an amount which is sufficient to suppress growth of mycobacteria associated with the hypersensitivity pneumonitis in the metalworking fluid for at least 48 hours; and (b) producing the shaped metal article from the metal workpiece while supplying the metalworking fluid to the interface wherein the copper complex and isothiazolone mixture in the metalworking fluid enables the metal-grinding machinist to produce the shaped metal article with the reduced risk of the hypersensitivity pneumonitis.

In a further embodiment of the above methods, the isothiazolone mixture comprises 5-chloro-2-methyl-4-isothiazolin-3-one 2-methyl-4-isothiazolin-3-one, wherein the mixture is present in an amount which is less than is required for biocidal activity when the mixture is introduced into the metalworking fluid alone and wherein the copper complex provides more than 250 ppm, preferably about 500 ppm, of copper ion to the metalworking fluid.

In a preferred embodiment of any one of the above methods, the 5-chloro-2-methyl-4-isothiazolin-3-one and 2-methyl-4-isothiazolin-3-one are in a weight ratio of about 3 to 1. It is further preferable that the composition be mixed with the metalworking fluid to produce an amount of the isothiazolone mixture which is greater than about 7.5 ppm, preferably from about 15 ppm to about 21 ppm. The above methods are particularly efficacious against the mycobacteria *Mycobacterium immunogenum* which has a restriction fragment length polymorphism pattern produced by a DraI digest of *Mycobacterium immunogenum* DNA as shown in FIG. 1. In further embodiments of any one of the above methods, the copper complex provides about more than 250 ppm, preferably about 500 ppm, copper ion to the metalworking fluid. The composition used in any one of the above methods is efficacious even when introduced to MWFs in which the isothiazolone is incompatible with the metalworking fluid when the isothiazolone mixture is introduced into the metalworking fluid alone.

The present invention further provides a method for determining the presence or absence of an industrial metalworking fluid isolate of *Mycobacteria immunogenum* in a sample, which comprises (a) culturing the sample in a medium which supports growth of the isolate; (b) isolating genomic DNA from the isolate which grows in the culture; (c) digesting the genomic DNA with DraI restriction enzyme to produce large restriction fragments of the genomic DNA; (d) electrophoresising the large restriction fragments on a gel by pulse-field gel electrophoresis to produce a pattern of the large restriction fragments on the gel; and (e) analyzing the pattern of the large restriction fragments wherein a pattern as shown in FIG. 1 indicates the presence of the isolate in the sample. In a further embodiment, the medium comprises a biocide which comprises a mixture of isothiazolones.

The present invention further provides a method for determining the presence or absence of an industrial metalworking fluid isolate of *Mycobacteria immunogenum* in a sample, which comprises culturing the sample in a medium comprising a tryptic soy or Middlebrook 7H10 medium, wherein growth of the isolate in the medium in less than seven days at about 30° or 35° C. indicates the presence of the isolate in the industrial metalworking fluid. Preferably, the medium further includes Tween 80, glycerin, cyclohexamide, chloramphenicol, and gentimicin. It is particularly convenient to provide the assay as a kit wherein an agar containing the medium is provided as the substrate for growing the mycobacteria. The agar containing the medium can be provided on petri dishes or the like or in a vial as an agar slant.

OBJECTS

The object of the present invention is to provide a method which reduces the risk that a metalworking machinist will contract hypersensitivity pneumonitis a metalworking environment.

A further object of the present invention is to provide a method of industrial metal grinding for producing shaped metal articles wherein the risk of a metal-grinding machinist contracting hypersensitivity pneumonitis is reduced.

A particular object of the present invention is to provide a method in which growth of *Mycobacterium immunogenum* in metalworking fluids is suppressed.

These and other objects of the present invention will become increasingly apparent with reference to the following drawings and preferred embodiments.

DETAILED DESCRIPTION OF THE INVENTION

Figure 1:
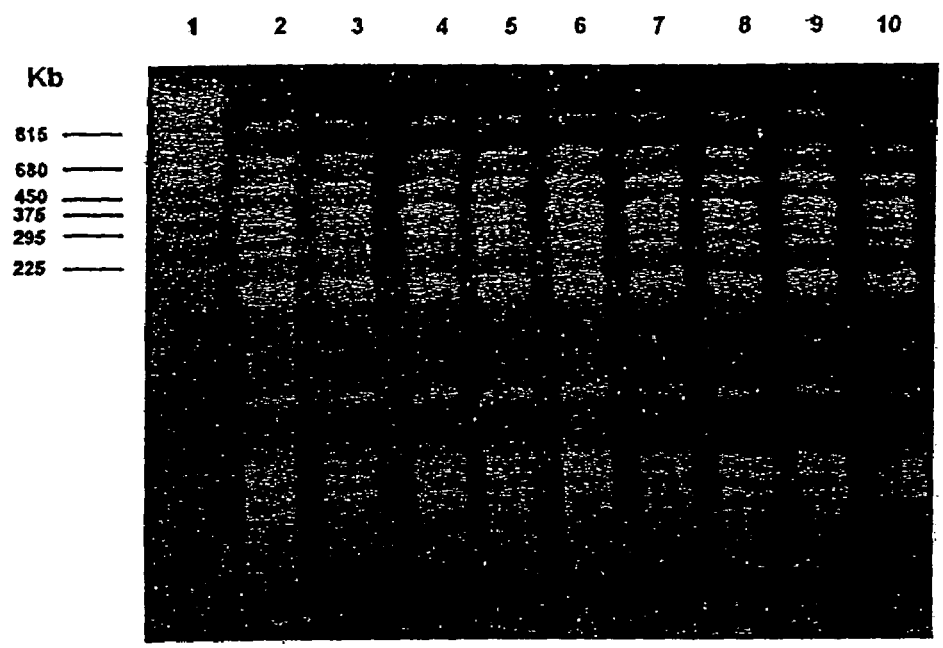
FIG. 1 shows a pulse-field gel electrophoresis (PFGE) pattern of *Mycobacteria immunogenum* from MWF from different metalworking plants. The chromosomal DNA was digested with DraI. Lanes: 1 yeast DNA standards; isolates from MWF in a plant in: 2, Ohio; 3, Illinois; 4, Indiana; 5, Wisconsin; 6, Illinois; 7, Wisconsin; 8, Indiana; 9, Michigan; and, 10, New York.

All patents, patent applications, government publications, government regulations, and literature references cited in this specification are hereby incorporated herein by reference in their entirety. In case of conflict, the present description, including definitions, will control.

U.S. Pat. No. 4,608,183 to Rossmoore discloses novel antimicrobial or biocidal mixtures comprising disodium monocopper citrate (MCC) and one or more isothiazolones which in the mixture synergistically suppress growth of many species of bacteria and fungi in metalworking fluids (MWF) over a long period of time. The mixtures were found to be particularly useful for treating MWFs wherein it was desired to confer long duration antimicrobial activity to the MWF even when the isothiazolones were at a concentration which if provided to the MWF without the MCC would not have been biocidal. Rossmoore (Intl. Biodeter. 26: 225–235 (1990) and Sondossi et al. (Intl. Biodeter. Biodeg. 32: 243–261 (1993) describe the interaction of isothiazolones and copper and the factors involved in the biocidal activities of isothiazolone mixtures. However, in spite of the widespread use of these mixtures to suppress microbial growth in MWFS, a recently characterized disease, hypersensitivity pneumonia, has emerged and is now a problem in the machine industry. More recently, a particular genotype of *Mycobacterium immunogenum* (MWF genotype) has been determined to be the etiological agent for hypersensitivity pneumonia (Wallace, Jr. et al., Appl. Environ. Microbiol. 68: 5580–5584 (2002).

I have discovered that contamination of MWF with the MWF genotype of *Mycobacterium immunogenum* can be controlled when a copper metal complex such as the preferred disodium monocopper citrate (MCC) is provided to the MWF in a mixture which comprises one or more isothiazolones or is provided to the MWF prior to the addition of the isothiazolones. The mixture suppresses the growth of the MWF genotype in the MWF. Suppression of mycobacteria growth is particularly efficacious when the copper metal complex is provided at a concentration greater than 250 ppm, preferably, at a concentration of about 500 ppm or more and the isothoazolone is provided at a concentration greater than 7.5 ppm, preferably at a concentration of about 15 ppm or more. In addition, MWFs containing the copper metal complex in an amount greater than 250 ppm, for example 500 ppm, stabilizes the isothiazolones for at least 48 hours.

As used herein, the term "suppression" when referring to mycobacteria growth in MWF means any one of the following activities: limiting the growth of the mycobacteria, inhibiting the growth of the mycobacteria, stopping the growth of the mycobacteria, inactivating the mycobacteria, or killing the mycobacteria.

The time in which the copper metal complex is added to the MWF relative to the time the isothiazolones are added to the MWF determines whether growth of the *Mycobacterium immunogenum* MWF genotype is suppressed. It was observed that adding MCC to a MWF 24 hours after the isothiazolones had been added to the MWF was ineffective at suppressing growth of the *Mycobacterium immunogenum* genotype. Thus, for proper supression of mycobacteria growth in the MWF, the copper metal complex should be added to a MWF within 24 hours of addition of the isothiazolones. However, to ensure effective suppression of mycobacteria growth, it is preferable that the copper metal complex be added to the MWF prior to the addition of the isothiazolones. Most preferably, the copper metal complex is added to the MWF at the same time the isothiazolones are added to the MWF. Therefore, in the most preferred embodiment, a mixture is provided as a single product which contains both the copper metal complex and the isothiazolones. The product provides a simple and convenient means for treating MWFs to suppress growth of the mycobacteria. A product comprising a mixture of both the copper metal complex and the isothiazolone is preferred because it prevents the occurrence of situations in which the isothiazolones are added to the MWF before the copper metal complex is added to be avoided. In other words, the mixture of copper metal complex and isothiazones ensures that the MWF contains both the copper metal complex and the isothiazones and that the isothiazolones were not added to the MWF prior to the copper metal complex.

The above mixture was further discovered to be efficacious even in MWFs which are incompatible with isothiazolones. That is, the MWF contains one or more components or variables which interfere with the antimicrobial activity of the isothiazolones, either partially or substantially reducing the efficacy of the isothiazolones to suppress growth of microorganisms (bacteria, fungi, and mycobacteria). In some instances this is interference is effected by various components in the MWF which facilitate conversion of isothiazolones from a chlorinated form to an unchlorinated form. Incompatibility of a MWF for isothiazolones can be effected by such variables as high pH-values (greater than about 8.5) or low pH-values (less than about 5.0); high temperatures (greater than about 40° C.); various reducing and oxidizing substances such as hypochloride, bisulfite or $H_2S$, cysteine, and the like; and, various strong nucleophilic substances (depending on pH and temperature) such as ammonia, primary and secondary amines, sulfides, and the like. Thus, the above mixture can be used to suppress the growth of the *Mycobacterium immunogenum* isolate even in MWFs which are incompatible with biocides comprising isothiazolones.

As shown in Examples 1–4, the copper metal complex must be added to the MWF in the appropriate amount and before adding the isothiazolones in the appropriate amount to the MWF. This is necessary in order for the isothiazolones to be stablized in the presence of nucleophiles which may be present in the MWF and which in turn maintains the efficacy of the composition against the mycobacteria. However, there has been a practical difficulty in guaranteeing that the copper metal complex will be present in industrial MWF systems when needed and at the appropriate amount. This is because even though written protocols have been provided with the metal copper complex and isothiazolones which explain the need for adding the copper metal complex to the MWF before the isothiazolones are added to the MWF, the copper metal complex is often not added to the MWF until after the isothiazolones have been added to the MWF and that is even when it is added to the MWF before there is both physical and chemical depletion of the copper in the MWF preventing its appropriate action. Therefore, in a preferred embodiment of the present invention, a composition is provided which comprises a mixture of the copper metal complex and the isothiazolones, each in an amount which enables the composition when added to a MWF to suppress growth of mycobacteria in the MWF, in particular the MWF isolate of *Mycobacterium immunogenum*.

The preferred composition avoids the above practical difficulty wherein the isothiazolones are added to a MWF before the copper metal complex is added to a MWF. The preferred composition can be provided in a single container which contains both the copper metal complex and the isothiazolones, each in an amount appropriate for treating a particular volume of MWF. In other words, the amount of composition in each container is sufficient to treat a particular volume of MWF. In practice, the user measures out from the container the appropriate amount of composition to be added to a particular volume of MWF to suppress growth of mycobacteria in the particular volume of MWF. For particularly large volumes of MWF, several containers of the composition might be added to the MWF to provide the proper amount of composition to suppress growth of the mycobacteria in the MWF. Preferably, the composition is provided in a concentrated form such as 2×, 5×, 10×, or the like. The concentrated form facilitates storage and handling of the composition. In another embodiment, the copper metal complex and isothiazolones are provided in separate containers with instructions that the copper metal complex and isothiazolones are mixed before adding to the MWF. This can be accomplished by the user measuring out the proper amounts of each for a particular volume of MWF, mixing them together in a vessel, and then adding the mixture in the vessel to the MWF. A mixing vessel can be included with the separately provided copper metal complex and isothiazolones.

The preferred copper metal complex is disodium monocopper (II) citrate (MCC) which is available as a concentrated commercial preparation from Coolant Control, Inc., Cincinnati, Ohio. Analysis via the iodide reduction method revealed a concentration of 1 mole/liter of Cu ion. The preparation was sterilized by passage through an 0.22 µm membrane filter. Copper containing compounds from Coolant Control, Inc. which are sold as enhancers for isothiazolone-based biocides include CUPRISAN, CITROXYL, and OXCEDOT O-50 (disodium monocopper (II) citrate).

Isothiazolones are frequently provided as a mixture of isothiazolones. For example, chloromethylisothiazolone (CMIT) is a mixture of 5-chloro-2-methyl-4-isothiazolin-3-one and 2-methyl-4-isothiazolin which is available under the trademark KATHON from Rohm and Haas of Philadelphia, Pa. KATHON includes KATHON 893 and KATHON 886 which are also available from Coolant Controls, Inc. In virgin KATHON, the ration of chlorinated to unchlorinated isothiazolones is about 3 to 1. The chlorinated form is the most active component of the isothiazolone mixture and it is also the most nucleophile sensitive. In many MWFs the ratio shifts over time towards the unchlorinated form because of reduction by one or more components which might be present in the MWF. The MCC appears to inhibit the dechlorination of the KATHON.

*Mycobacterium immunogenum* isolated from a MWF has been deposited at the American Type Culture Collection, 10801 University Boulevard, Manassas, Va. as ATCC 700506 and the Deutsche Sammlung von Mikroorganismen und Zellkulturen GmbH, Braunschweig, Germany as DSMZ 8223. The phenotypic characteristics of the isolate is described in (Moore et al., AIHJ 61: 205–213 (2000); Wilson et al., Intl. J. Syst. Evol. Microbiol. 51: 1751–1764 (2001)). Briefly, the *Mycobacterium immunogenum* isolate has a typical morphology with acid-fast staining, the absence of pigmentation, growth on tryptic soy and Middlebrook 7H10 agar in less than seven days at 30° and 35° C., no growth at 45° C., mycolic acid production, growth on MacConkey agar without crystal violet, negative for iron up-take and nitrate reductase, and a positive 3-d arylsulfatase reaction. The isolate cannot utilize citrate, D-glucitol (D-sorbitol), i-myo-inositol, and D-mannitol as sole carbon sources. The isolate is resistant to amikacin (MIC 128 µg/mL), cefinetazole (MIC 64 µg/mL), cefoxitin (MIC 64 µg/mL), ciprofloxacin (MIC >16 µg/mL), doxyxycline (MIC >128 µg/mL), imipenem (MIC 16 µg/mL), sulfamethoxazole (MIC >64 µg/mL), and tobramycin (MIC >16 µg/mL). The isolate is unable to grow on Löwenstein-Jensen medium containing 5% NaCl at 35° C. However, the isolate exhibits 25 to 50% growth in the presence of 5% NaCl at 30° C. compared with control growth on Löwenstein-Jensen medium containing 5% NaCl at 35° C. General methods for identifying mycobacteria include Telenti et al., J. Clin. Microbiol. 31: 175–178 (1993); Wallace Jr. et al., J. Clin. Microbiol. 31: 2697–2701 (1993); Wallace Jr. et al., J. Clin. Micobiol. 31: 3231–3239 (1993); and, Steingrube et al., J. Clin. Microbiol. 33: 149–153 (1995). The methods described in the above have been used to characterize the MWF isolate disclosed herein.

*Mycobacterium immunogenum* isolated from MWFs has further been described in Wallace Jr. et al., Appl. Environ. Microbiol. 68: 5580–5584 (2002) which discloses that *Mycobacterium immunogenum* isolated from MWFs from a plurality of locations across the United States all have a particular genotype. These MWF isolates were found to have an identical DraI restriction enzyme pattern when their genomic DNA was digested with DraI and resolved by pulse-field gel electrophoresis (See FIG. 1). This DraI restriction enzyme pattern distinguishes the MWF isolates from *Mycobacterium immunogenum* isolated from other sources.

The above characteristics of the MWF isolate of *Mycobacterium immunogenum* can be used to design a diagnostic assay for determining the presence of the isolate in a MWF. For example, a sample from a MWF is incubated in a tryptic soy or Middlebrook 7H10 medium which preferably further includes Tween 80, glycerin, cyclohexamide, chloramphenicol, and gentimicin to suppress growth of unwanted bacteria and fungi. Growth of the isolate in the medium indicates the presence of the isolate in the industrial metalworking fluid. Particularly, when multiple samples are assayed and there is growth in less than seven days for the samples incubated at about 30° and 35° C. and no growth for the samples incubated at about 45° C. The assay can further include positive and negative controls. The assay can be performed in liquid medium, however, it is preferable to perform the assay on an agar support which comprises the medium. For example, a sample of MWF is inoculated onto agar plates or slants which comprise the medium. The inoculated plates or slants are covered and incubated at the appropriate temperature. Detection of the mycoplasma is by visually observing by eye colonies of the mycobacteria which can have either a rough or smooth morphology. Alternatively, the mycobacteria can be visualized by acid-fast staining.

The above assay can be provided as a kit. In one embodiment, a kit is provided in which agar comprising the above medium is provided as an agar slant in a container which has a lid (screw cap or snap-top). This embodiment of the kit enables the user to inoculate the agar slant in the container, cover the container with the lid, and incubate the container at the appropriate temperature with monitoring for growth of the mycobacteria. In further embodiments, the kit can include a sample applicator. In a second embodiment, a kit is provided in which flexible plastic strips to which absorbant material such as filter paper comprising the above medium is attached. A MWF sample is inoculated to the filter paper on the strip or the filter paper on the strip is inoculated by dipping into the MWF. Afterwards, the inoculated strip is incubated at the appropriate temperature and monitored for growth of the mycobacteria. In a third embodiment, a kit is provided in which a slide is afixed to the inner surface of a lid to a container with an opening. When the lid is fastened to the container, the slide extends from the lid into the opening of the container. The slide comprises on its surface the above medium in agar or absorbant material. A MWF sample is inoculated to the slide or the slide is inoculated by dipping into the MWF. The slide is then inserted into the opening of the container and the lid fastened. The container with the slide therein is incubated at the appropriate temperature with monitoring for growth of the mycobacteria. The above kits can be provided with the above product comprising the mixture of the copper metal complex, preferably the MCC, and isothiazolones, preferably the mixture of 5-chloro-2-methyl-4-isothiazolin-3-one and 2-methyl-4-isothiazolin.

The following examples are intended to promote a further understanding of the present invention.

EXAMPLES 1 and 2

This example illustrates that in order for the mixture to be efficacious against *Mycobacterium immunogenum* MWF isolates, the copper activity from the copper metal complex needs to be present in industrial MWF systems either prior to addition of the isothiazolones or the copper metal complex is mixed with the isothiazolones and the mixture is added to the MWF. When the isothiazolones are added 24 hours before the copper metal complex is added, there is no protection. In spite of instructions to on-site workforces about the order and time of addition of the copper metal complex and the isothiazolones, frequently the isothiazolones are added before the copper metal complex. The result is no biocidal protection against mycobacteria.

The MWFs selected were fluids which had evidence of CMIT incompatibility. The MCC was added to the MWFs 24 hours before the CMIT was added; 24 hours after the CMIT was added; or in a mixture with the CMIT. This was done for each concentration of CMIT (7.5 and 15 ppm) and MCC (250 and 500 ppm). Controls consisted of no biocide and CMIT at 7.5 and 15 ppm. Stability of the isothiazolones was evaluated at time 0 and then after 24 and 48 hours by standard methods for detecting isothiazones. Plating for mycobacteria kill was performed with aliquots from time 0 and 48 hours.

Plating was performed on 100 mm petri dishes containing 20 mL of an appropriate agar. Two different formulations, both based on Plate Count Agar (standard methods for waste and waste water). The medium for recovery of *Mycobacterium immunogenum* is nutritionally supplemented with TWEEN 80 and glycerin and has three antibiotics (cyclohexamide, chloramphenicol, and gentimicin) to inhibit fungi and unwanted bacteria. This medium with agar is referred to herein as "Mycoagar."

The preferred embodiment of the present invention is a combination package containing both CMIT and MCC. Tables 1 and 2 show that for stability of the CMIT and for suppressing growth of mycobacteria, the MCC must be present before the CMIT is added to the MWF or in a mixture with the CMIT. The results further show that for efficacious biocidal activity against mycoplasma, the amount of MCC should be greater than 250 ppm, preferably about 500 ppm or more, and the amount of CMIT should be greater than 7.5 ppm, preferably 15 ppm or more. Note that the MCC significantly enhanced the stability of the CMIT when it was provided at a concentration of about 500 ppm to the MWF before addition of the CMIT or in a mixture with the CMIT.

TABLE 1

Stability of CMIT in MWF

| Biocide and Concentration | ppm CMIT Time After Addition | | | | | |
|---|---|---|---|---|---|---|
| | 0 hr | | 24 hr | | 48 hr | |
| | MWF 1 | MWF 2 | MWF 1 | MWF 2 | MWF 1 | MWF 2 |
| No biocide | <1 | <1 | <1 | <1 | <1 | <1 |
| 7.5 ppm CMIT | 8.3 | 8.4 | 4.2 | 4.5 | 3.2 | 1.8 |
| 15 ppm CMIT | 14.8 | 16.3 | 5.8 | 8.5 | 2.0 | 2.8 |
| 7.5 ppm CMIT/250 ppm Cu citrate added together | 7.7 | 8.1 | 7.0 | 7.7 | 5.3 | 6.5 |
| 15 ppm CMIT/500 ppm Cu citrate added together | 13.7 | 14.0 | 13.4 | 13.5 | 10.2 | 12.3 |
| 7.5 ppm CMIT added 24 hrs before 250 ppm Cu citrate added | 8.3 | 4.8 | 3.7 | 3.1 | 3.3 | 2.9 |
| 15 ppm CMIT added 24 hrs before 500 ppm Cu citrate added | 6.6 | 7.1 | 6.5 | 5.8 | 1.9 | 4.4 |
| 7.5 ppm CMIT added 24 hrs after 250 ppm Cu citrate added | 8.0 | 7.7 | 7.9 | 6.1 | 6.7 | 4.9 |
| 15 ppm CMIT added 24 hrs after 500 ppm Cu citrate added | 14.6 | 14.5 | 13.7 | 13.3 | 12.3 | 11.7 |

CMIT: chloromethylisothiazolone (1.5% active ingredient)
Stability indicated by bold-faced type

TABLE 2

Anti-Mycobacterial Activity

| Biocide and Concentration | Mycobacteria/mL | | | |
|---|---|---|---|---|
| | MWF 1 | | MWF 2 | |
| | 0 hr | 48 hr | 0 hr | 48 hr |
| No biocide | $1.0 \times 10^6$ | $1.0 \times 10^6$ | $3.5 \times 10^5$ | $3.0 \times 10^6$ |
| 7.5 ppm CMIT | $1.0 \times 10^6$ | $1.9 \times 10^5$ | $3.5 \times 10^5$ | $1.3 \times 10^5$ |
| 15 ppm CMIT | $1.0 \times 10^6$ | $4.5 \times 10^3$ | $3.5 \times 10^5$ | $4.5 \times 10^3$ |
| 7.5 ppm CMIT/250 ppm Cu citrate added together | $1.0 \times 10^6$ | $1.2 \times 10^4$ | $3.5 \times 10^5$ | $8.5 \times 10^3$ |
| 15 ppm CMIT/500 ppm Cu citrate added together | $1.0 \times 10^6$ | <100 | <100 | <100 |
| 7.5 ppm CMIT added 24 hrs before 250 ppm Cu citrate added | $1.0 \times 10^6$ | $1.4 \times 10^5$ | $3.5 \times 10^5$ | $1.6 \times 10^5$ |
| 15 ppm CMIT added 24 hrs before 500 ppm Cu citrate added | $1.0 \times 10^6$ | $5.0 \times 10^3$ | $3.5 \times 10^5$ | $4.5 \times 10^3$ |
| 7.5 ppm CMIT added 24 hrs after 250 ppm Cu citrate added | $1.0 \times 10^6$ | $1.2 \times 10^4$ | $3.5 \times 10^5$ | $8.0 \times 10^3$ |
| 15 ppm CMIT added 24 hrs after 500 ppm Cu citrate added | $1.0 \times 10^6$ | <100 | $3.5 \times 10^5$ | <100 |

CHIT: chloromethylisothiazolone (1.5% active ingredient)
Effective kill indicated by bold-faced type EXAMPLES 3 and 4

In this example, the amount of copper citrate was decreased in a static system to reproduce the potential loss of copper citrate from MWFs in a metalworking plant's recirculating system.

The MWFs selected were fluids which had evidence of CMIT incompatibility. The MCC was added to the MWFs 24 hours before the CMIT was added at 15 ppm. Stability was evaluated at time 0 and then after 24 and 48 hours by chemical analysis. Plating for mycobacteria kill was performed with aliquots from time O and after 48 hours.

As shown in Tables 3 and 4, the amount of copper which is needed for stability and effective suppression of mycobacteria growth is greater than 250 ppm, preferably about 500 ppm or more.

This example further demonstrates the ability of the 15 ppm CMIT/500 ppm MCC of the present invention to control the *Mycobacterium immunogenum* isolate which is the etiological agent for HP among machine tool workers. In addition, the CMIT in the mixture of the present invention has increased stability over CMIT mixtures which do not contain the MCC.

TABLE 3

Stability of CHIT in MWF

| | ppm CMIT Time After Addition | | | | | |
|---|---|---|---|---|---|---|
| | 0 hr | | 24 hr | | 48 hr | |
| Concentration of Cu Citrate in Biocide | MWF 1 | MWF 2 | MWF 1 | MWF 2 | MWF 1 | MWF 2 |
| 15 ppm CMIT added 24 hrs after 125 ppm Cu citrate added | 13.8 | 12.9 | 2.4 | 2.2 | 1.8 | 0.8 |
| 15 ppm CMIT added 24 hrs after 250 ppm Cu citrate added | 13.7 | 13.1 | 2.9 | 2.5 | 1.2 | 0.8 |
| 15 ppm CMIT added 24 hrs after 500 ppm Cu citrate added | 14.6 | 14.5 | 13.7 | 13.3 | 12.3 | 11.7 |

CMIT: chloromethylisothiazolone (1.5% active ingredient)
Stability indicated by bold-faced type

TABLE 4

Anti-Mycobacterial Activity

| | Mycobacteria/mL | | | |
|---|---|---|---|---|
| | 0 hr | | 24 hr | |
| Concentration of Cu Citrate in Biocide | MWF 1 | MWF 2 | MWF 1 | MWF 2 |
| 15 ppm CMIT added 24 hrs before 125 ppm Cu citrate added | $2.0 \times 10^6$ | $4.5 \times 10^6$ | $1.0 \times 10^4$ | $1.0 \times 10^4$ |
| 15 ppm CMIT added 24 hrs after 250 ppm Cu citrate added | $1.5 \times 10^6$ | $1.5 \times 10^6$ | $2.5 \times 10^3$ | $1.5 \times 10^4$ |
| 15 ppm CMIT added 24 hrs after 500 ppm Cu citrate added | $1.0 \times 10^6$ | $3.5 \times 10^5$ | <100 | <100 |

CMIT: chloromethylisothiazolone (1.5% active ingredient)
Effective kill indicated by bold-faced type

TABLE 5

| Sample | Total Plate Count Bacterial/mL | Total Fungal Count Fungi/mL | Total Myco Count Myco/mL | AFB Stain |
|---|---|---|---|---|
| V1 | <1 | <10 | $1.0 \times 10^3$ | Very high |
| V2 | <1 | <10 | $4.0 \times 10^3$ | Very high |
| V3 | <1 | <10 | <1 | Moderate |
| V4 | <1 | <10 | $2.5 \times 10^2$ | Very high |

AFB: Pellet Stain Counts include live and dead mycobacteria

| | | ppm KATHON | | |
|---|---|---|---|---|
| Sample | ppm GROTAN | Unchlorinated | Chlorinated | Total |
| V1 | 1837 | 0 | 0 | 0 |
| V2 | 1402 | 7.2 | 15.2 | 22.4 |
| V3 | 1119 | 6.3 | 15.5 | 21.8 |
| V4 | 1837 | 5.4 | 13.8 | 19.2 |

EXAMPLES 5–8

The data shown in the following tables was generated from samples from the field already treated with two biocides, GROTON (a formalydehyde condensate available from Troy Corporation, Florham Park, N.J.) and KATHON (CMIT). Each table shows the results for samples obtained from a particular source. The tables show the survival of mycobacteria in the presence of CMIT alone. Note that there are two columns for the CMIT: chlorinated and unchlorinated. The ratio of chlorinated to unchlorinated in virgin CMIT is 3 to 1. The chlorinated form is the most active component of the CMIT and it is the most nucleophile sensitive. When the ratio of chorinated to unchlorinated is less than 3 to 1, it is assumed that the chlorinated moiety has been reduced by one or more components in the MWF.

The tables also show that the total plate count for bacteria for all samples except for those labeled J were less than 1. The J samples had no detectable biocides whereas all the other samples had substantial levels of GROTAN and evidence of CMIT use. GROTAN and CMIT are compatible biocides.

The data shown in this example demonstrate that mycobacteria are more resistant to CMIT than other bacteria which can be controlled by lower levels of CMIT.

TABLE 6

| Sample | Total Plate Count Bacterial/mL | Total Fungal Count Fungi/mL | Total Myco Count Myco/mL | AFB Stain |
|---|---|---|---|---|
| V1 | <1 | <10 | $7.5 \times 10^5$ | Moderate |
| V2 | <1 | $4.0 \times 10^1$ | $8.5 \times 10^5$ | Moderate |
| V3 | <1 | $3.0 \times 10^1$ | $1.0 \times 10^4$ | Low/Moderate |
| V4 | <1 | <10 | $2.0 \times 10^4$ | Very high |
| E | <1 | $1.0 \times 10^1$ | $2.0 \times 10^6$ | Moderate |
| H$_2$O Solution | <1 | <10 | <1 | Negative |
| | <1 | <10 | <1 | Negative |

AFB: Pellet Stain Counts include live and dead mycobacteria

| | | ppm KATHON | | |
|---|---|---|---|---|
| Sample | ppm GROTAN | Unchlorinated | Chlorinated | Total |
| V1 | 2878 | 5.3 | 0.7 | 6 |
| V2 | 2518 | 4.1 | 0.1 | 4.2 |
| V3 | 3058 | 1.7 | 0.2 | 1.9 |
| V4 | 2518 | 5.3 | 0.5 | 5.8 |
| E | 2698 | 0 | 0 | 0 |
| H$_2$O | 0 | 0 | 0 | 0 |
| Solution | 2698 | 0 | 0 | 0 |

TABLE 7

| Sample | Total Plate Count Bacterial/mL | Total Fungal Count Fungi/mL | Total Myco Count Myco/mL | AFB Stain |
|---|---|---|---|---|
| V1 | <1 | <10 | $2.0 \times 10^5$ | Very High |
| V2 | <1 | <10 | $2.5 \times 10^5$ | Very high |
| E | <1 | <10 | $8.0 \times 10^4$ | Moderate |
| J | $3.5 \times 10^4$ | <10 | <1 | Very high |

AFB: Pellet Stain Counts include live and dead mycobacteria

| | | ppm KATHON | | |
|---|---|---|---|---|
| Sample | ppm GROTAN | Unchlorinated | Chlorinated | Total |
| V1 | 2297 | 11.2 | 1.9 | 13.1 |
| V2 | 2702 | 8 | 1.6 | 9.6 |
| E | 3513 | 7.1 | 1.4 | 8.5 |
| J | 0 | 0 | 0 | 0 |

TABLE 8

| Sample | Total Plate Count Bacterial/mL | Total Fungal Count Fungi/mL | Total Myco Count Myco/mL | AFB Stain |
|---|---|---|---|---|
| V1 | <1 | <10 | $1.0 \times 10^5$ | Very high |
| V2 | <1 | <10 | $4.0 \times 10^5$ | Very high |
| V3 | <1 | <10 | $2.0 \times 10^5$ | Moderate/high |
| V4 | <1 | <10 | $1.0 \times 10^5$ | Very high |
| E | <1 | <10 | $2.5 \times 10^5$ | Moderate/high |
| J | $1.5 \times 10^7$ | $1.1 \times 10^2$ | <1 | Moderate |

AFB: Pellet Stain Counts include live and dead mycobacteria

| | | ppm KATHON | | |
|---|---|---|---|---|
| Sample | ppm GROTAN | Unchlorinated | Chlorinated | Total |
| V1 | 1417 | 9.5 | 1.8 | 11.3 |
| V2 | 2083 | 7.1 | 1.3 | 8.4 |
| V3 | 2000 | 0 | 0 | 0 |
| V4 | 2417 | 8 | 1.3 | 9.3 |
| E | 2000 | 7.5 | 1 | 8.5 |
| J | 0 | 0 | 0 | 0 |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for reducing a risk that a person in a metalworking environment will contract hypersensitivity pneumonitis caused by *Mycobacterium immunogenum* which is present in the environment, which comprises:
   (a) providing a composition comprising a copper complex comprising disodium monocopper (II) citrate and an isothiazolone mixture wherein the copper complex provides more than about 250 ppm of copper ion to a metalworking fluid, wherein the isothiazolone mixture comprises 5-chloro-2methyl-4-isothiazolin-3-one and 2-methyl-4-isothiazolin-3-one, wherein the isothiazolone mixture is present in an amount which is less than is required for biocidal activity when the mixture is introduced into the metalworking fluid alone;
   (b) adding the composition to the metalworking fluid, which contains components from use of the fluid which interfere with the antimicrobial activity of the isothiazolone mixture in the environment, in an amount which is sufficient to suppress the growth of the *Mycobacterium immunogenum* in the metalworking fluid for at least 48 hours wherein the metalworking fluid containing the composition is monitored for the *Mycobacterium immunogenum*; and
   (c) exposing the person to the metalworking environment, wherein suppression of the growth of the *Mycobacterium immunogenum* in the metalworking fluid by the composition reduces the risk that the person will contract the hypersensitivity pneumonitis.

2. The method of claim 1 wherein the 5-chloro-2methyl-4-isothiazolin-3-one and 2methyl-4-isothiazolin-3-one are in a weight ratio of about 3 to 1.

3. The method of claim 1 wherein the composition is mixed with the metalworking fluid to produce an amount of the isothiazolone mixture which is from about 15 ppm to about 21 ppm.

4. The method of claim 1 wherein the *Mycobacterium immunogenum* has a restriction fragment length polymorphism pattern produced by a DraI digest of *Mycobacterium immunogenum* DNA as shown in FIG. 1.

5. The method of claim 1 wherein the isothiazolone mixture is incompatible with the metalworking fluid when the isothiazolone mixture is introduced into the metalworking fluid alone.

* * * * *

UNITED STATES PATENT AND TRADEMARK OFFICE
CERTIFICATE OF CORRECTION

PATENT NO. : 7,147,824 B2
APPLICATION NO. : 11/242293
DATED : December 12, 2006
INVENTOR(S) : Harold W. Rossmoore It is certified that error appears in the above-identified patent and that said Letters Patent is hereby corrected as shown below:

Column 8, line 54, "cefinetazole" should be --cefmetazole--.
Column 11, line 65, Table 2, "CHIT" should be --CMIT--.
Column 13, line 1, Table 3, "CHIT" should be --CMIT--.

Signed and Sealed this

Thirteenth Day of November, 2007

JON W. DUDAS
*Director of the United States Patent and Trademark Office*